United States Patent [19]

Foster et al.

[11] Patent Number: 5,766,921

[45] Date of Patent: Jun. 16, 1998

[54] HYBRID PROTEIN C

[75] Inventors: Donald C. Foster; Richard D. Holly, both of Seattle, Wash.

[73] Assignee: Zymogenetics, Inc., Seattle, Wash.

[21] Appl. No.: 318,579

[22] Filed: Oct. 5, 1994

Related U.S. Application Data

[63] Continuation of Ser. No. 515,378, Apr. 27, 1990, abandoned, which is a continuation-in-part of Ser. No. 458,856, Dec. 29, 1989, abandoned.

[51] Int. Cl.$^6$ .................... C12N 15/00; C12N 5/00; C12P 21/06; C07H 21/02
[52] U.S. Cl. .................... 435/240.2; 435/172.3; 435/69.1; 536/23.1; 536/23.2
[58] Field of Search .................... 536/23.1; 435/240.2, 435/172.3

[56] References Cited

U.S. PATENT DOCUMENTS

| 4,711,848 | 12/1987 | Insely et al. |
| 4,775,624 | 10/1988 | Bang et al. |
| 4,902,614 | 2/1990 | Wakabayashi et al. |
| 5,077,024 | 12/1991 | Brake et al. |

FOREIGN PATENT DOCUMENTS

| 215548 | 3/1987 | European Pat. Off. |
| 245949 | 11/1987 | European Pat. Off. |
| 0266190 | 5/1988 | European Pat. Off. |
| 0296413 | 12/1988 | European Pat. Off. |
| 318201 | 5/1989 | European Pat. Off. |
| 0319944 | 6/1989 | European Pat. Off. |
| 319312 | 6/1989 | European Pat. Off. |
| 323149 | 7/1989 | European Pat. Off. |
| 327377 | 8/1989 | European Pat. Off. |
| 352651 | 1/1990 | European Pat. Off. |
| 354504 | 2/1990 | European Pat. Off. |
| 8810295 | 12/1988 | WIPO. |
| 8912685 | 12/1989 | WIPO. |
| 9010649 | 9/1990 | WIPO. |

OTHER PUBLICATIONS

Creighton, *Prog. Biophys. Molec. Biol.* 33:231–297 (1978).
Brot et al., *Arch. Biochem. Biophys.* 223:221–281 (1983).
Wilkinson, *Prac. Protein Chem.,* (ed.) A. Darbre, pp. 121–148, (1986).
Heeb et al., *J. Biol. Chem.* 263:1163–1161 (1988).
Yan and Grinnell, *Fed. Proc.* 46:2243 (1987).
Yan et al., *FASEB J.* 2:A1412 (1988).
Grinnell et al., *Bio/Technology* 5:1189–1192 (1987).
Ehrlich et al., *J. Biol. Chem.* 264:14298–14304 (1989).
Thomas et al., *Science* 241:226–230 (1980).
Marx, *Science* 235:285–286 (1987).
Bathurst et al., *Science* 235:248–350 (1987).
Dmochowska et al., *Cell* 50:573:584 (1987).
Fuller et al., in Leive ed., *Microbiology: 1986* 273–278.
Taylor et al., *J. Clin. Invest.* 79:918–925 (1987).
Sakata et al., *Proc. Natl. Acad. Sci. USA* 82:1121–1125 (1985).
van Hinsbergh et al., *Blood* 65:444–451 (1985).
Comp and Esmon. *J. Clin. Invest.* 68:1221–1228 (1981).
Foster et al., *Proc. Natl. Acad. Sci. USA* 81:4766–4770 (1984).
Long et al., *Proc. Natl. Acad. Sci. USA* 82:4673–4677 (1985).
Foster et al., *Proc. Natl. Acad. Sci. USA* 82:4673–4677 (1985).
Beckmann et al., *Fed. Proc.* 44:1069 (1985).
Ehrlich et al., *Blood* 70:386a (1987).
Okayama et al., *Mol. cell. Biol.* 2:161–170 (1982).
Miessner et al., *Proc. Natl. Acad. Sci. USA* 84:4171–4175 (1987).
Walker et al. *Thrombosis Res.* 22: 321. 1981.
Long et al. *PNAS* 81: S653. 1984.
Kisiel et al. *Biochemistry* 16(26) : 5824. 1977.

*Primary Examiner*—Suzanne E. Ziska
*Attorney, Agent, or Firm*—Townsend and Townsend and Crew, LLP

[57] ABSTRACT

Human protein C molecules are modified to provide increased resistance to inactivation by human plasma factors while retaining substantially the biological activity of human protein C. The modifications are generally to the heavy chain of protein C, which chain may be substituted with a protein C heavy chain of non-human origin, such as bovine, yielding a chimeric protein C molecule. The human protein C heavy chain may also be modified to be human-like, in that at least one amino acid from a non-human sequence may be substituted for the corresponding residue(s) of the human sequence, thereby allowing the molecule to retain substantially human characteristics yet having increased resistance to inactivation. Also included are methods for producing the modified protein C molecules and pharmaceutical compositions thereof. The modified molecules, having an increased half-life in human plasma, are particularly useful for treating coagulation-related disorders, such as protein C deficiency or thrombosis, or for promoting fibrinolysis in a patient.

12 Claims, 8 Drawing Sheets

```
GGCTGTCATG GCGGCAGGAC GGCGAACTTG CAGTATCTCC ACGACCCGCC CCTGTGCCAG TGCCTCCAG
-42       -40                                    -30
ATG TGG CAG CTC ACA AGC CTG CTG CTG TTC GTG GCC ACC TGG GGA ATT TCC GGC
MET Trp Gln Leu Thr Ser Leu Leu Leu Phe Val Ala Thr Trp Gly Ile Ser Gly
            -20                                        -10
ACA CCA GCT CCT CTT GAC TCA GTG TTC TCC AGC AGC GAG CGT GCC CAC CAG GTG
Thr Pro Ala Pro Leu Asp Ser Val Phe Ser Ser Ser Glu Arg Ala His Gln Val
                -1  +1                                  10
CTG CGG ATC CGC AAA CGT GCC AAC TCC TTC CTG GAG GAG CTC CGT CAC AGC AGC
Leu Arg Ile Arg Lys Arg Ala Asn Ser Phe Leu Glu Glu Leu Arg His Ser Ser
                        20                                          30
CTG GAG CGG GAG TGC ATA GAG GAG ATC TGT GAC TTC GAG GAG GCC AAG GAA ATT
Leu Glu Arg Glu Cys Ile Glu Glu Ile Cys Asp Phe Glu Glu Ala Lys Glu Ile
                            40
TTC CAA AAT GTG GAT GAC ACA CTG GCC TTC TGG TCC AAG CAC GTC GAC GGT GAC
Phe Gln Asn Val Asp Asp Thr Leu Ala Phe Trp Ser Lys His Val Asp Gly Asp
        50                                  60
CAG TGC TTG GTC TTG CCC TTG GAG CAC CCG TGC GCC AGC CTG TGC TGG GGG CAC
Gln Cys Leu Val Leu Pro Leu Glu His Pro Cys Ala Ser Leu Cys Cys Gly His
            70                                      80
GGC ACG TGC ATC GAC GGC ATC GGC AGC TTC AGC TGC GAC TGC CGC AGC GGC TGG
Gly Thr Cys Ile Asp Gly Ile Gly Ser Phe Ser Cys Asp Cys Arg Ser Gly Trp
                    90                              ♦          100
GAG GGC CGC TTC TGC CAG CGC GAG GTG AGC TTC CTC AAT TGC TCG CTG GAC AAC
Glu Gly Arg Phe Cys Gln Arg Glu Val Ser Phe Leu Asn Cys Ser Leu Asp Asn
                            110                                     120
GGC GGC TGC ACG CAT TAC TGC CTA GAG GAG GTG GGC TGG CGG CGC TGT AGC TGT
Gly Gly Cys Thr His Tyr Cys Leu Glu Glu Val Gly Trp Arg Arg Cys Ser Cys
                            130
GCG CCT GGC TAC AAG CTG GGG GAC GAC CTC CTG CAG TGT CAC CCC GCA GTG AAG
Ala Pro Gly Tyr Lys Leu Gly Asp Asp Leu Leu Gln Cys His Pro Ala Val Lys
    140                                     150
TTC CCT TGT GGG ACG CCC TGG AAG GGG ATG GAG AAG AAG CGC AGT CAC CTG AAA
Phe Pro Cys Gly Arg Pro Trp Lys Gly Met Glu Lys Lys Arg Ser His Leu Lys
            160                                 ↓170
CGA GAC ACA GAA GAC CAA GAA GAC CAA GTA GAT CCG CGG CTC ATT GAT GGG AAG
Arg Asp Thr Glu Asp Gln Glu Asp Gln Val Asp Pro Arg Leu Ile Asp Gly Lys
                    180                                     190
ATG ACC AGG CGG GGA GAC ACC CCC TGG CAG GTG GTC CTG CTG GAC TCA AAG AAG
Met Thr Arg Arg Gly Asp Ser Pro Trp Gln Val Val Leu Leu Asp Ser Lys Lys
                            200                                     210
AAG CTG GCC TGC GGG GCA GTG CTC ATC CAC CCC TCC TGG GTG CTG ACA GCG GCC
Lys Leu Ala Cys Gly Ala Val Leu Ile His Pro Ser Trp Val Leu Thr Ala Ala
                            220
CAC TGC ATG GAT GAG TCC AAG AAG CTC CTT GTC AGG CTT GGA GAG TAT GAC CTG
His Cys Met Asp Glu Ser Lys Lys Leu Leu Val Arg Leu Gly Glu Tyr Asp Leu
        230                                     240
CGG CGC TGG GAG AAG TGG GAG CTG GAC CTG GAC ATC AAG GAG GTC TTC GTC CAC
Arg Arg Trp Glu Lys Trp Glu Leu Asp Leu Asp Ile Lys Glu Val Phe Val His
```

Fig. 1A

```
     ◆    250                                          260
CCC AAC TAC AGC AAG AGC ACC ACC GAC AAT GAC ATC GCA CTG CTG CAC CTG GCC
Pro Asn Tyr Ser Lys Ser Thr Thr Asp Asn Asp Ile Ala Leu Leu His Leu Ala
                        270                                  280
CAG CCC GCC ACC CTC TCG CAG ACC ATA GTG CCC ATC TGC CTC CCG GAC AGC GGC
Gln Pro Ala Thr Leu Ser Gln Thr Ile Val Pro Ile Cys Leu Pro Asp Ser Gly
                                290                                  300
CTT GCA GAG CGC GAG CTC AAT CAG GCC GGC CAG GAG ACC CTC GTG ACG GGC TGG
Leu Ala Glu Arg Glu Leu Asn Gln Ala Gly Gln Glu Thr Leu Val Thr Gly Trp
                                    310       ◆
GGC TAC CAC AGC AGC CGA GAG AAG GAG GCC AAG AGA AAC CGC ACC TTC GTC CTC
Gly Tyr His Ser Ser Arg Glu Lys Glu Ala Lys Arg Asn Arg Thr Phe Val Leu
    320                                  ◆ 330
AAC TTC ATC AAG ATT CCC GTG GTC CCG CAC AAT GAG TGC AGC GAG GTC ATG AGC
Asn Phe Ile Lys Ile Pro Val Val Pro His Asn Glu Cys Ser Glu Val Met Ser
                340                                  350
AAC ATG GTG TCT GAG AAC ATG CTG TGT GCG GGC ATC CTC GGG GAC CGG CAG GAT
Asn Met Val Ser Glu Asn Met Leu Cys Ala Gly Ile Leu Gly Asp Arg Gln Asp
                    360                                      370
GCC TGC GAG GGC GAC AGT GGG GGG CCC ATG GTC GCC TCC TTC CAC GGC ACC TGG
Ala Cys Glu Gly Asp Ser Gly Gly Pro Met Val Ala Ser Phe His Gly Thr Trp
                            380                                      390
TTC CTG GTG GGC CTG GTG AGC TGG GGT GAG GGC TGT GGG CTC CTT CAC AAC TAC
Phe Leu Val Gly Leu Val Ser Trp Gly Glu Gly Cys Gly Leu Leu His Asn Tyr
                                400
GGC GTT TAC ACC AAA GTC AGC CGC TAC CTC GAC TGG ATC CAT GGG CAC ATC AGA
Gly Val Tyr Thr Lys Val Ser Arg Tyr Leu Asp Trp Ile His Gly His Ile Arg
    410                                  419
GAC AAG GAA GCC CCC CAG AAG AGC TGG GCA CCT TAC CGACCCTCCG TGCAGGGCTG
Asp Lys Glu Ala Pro Gln Lys Ser Trp Ala Pro
GGCTTTTGCA TGGCAATGGA TGGGACATTA AAGGGACATG TAACAAGCAC ACCGGCCTGC TGTTCTGTCC
TTCCATCCCT CTTTTGGGCT CTTCTGGAGG GAAGTAACAT TTACTGAGCA CCTGTTGTAT GTCACATGCC
TTATGAATAG AATCTTAACT CCTAGAGCAA CTCTGTGGGG TGGGGAGGAG CAGATCCAAG TTTTGCGGGG
TCTAAAGCTG TGTGTGTTGA GGGGGATACT CTGTTTATGA AAAAGAATAA AAAACACAAC CACGAAAAAA
```

HEAVY CHAIN

```
HUMAN    DTEDQEDQVDPRLIDGKMTRRGDSPWQVVLLDSKKKLACGAVLIHPSW
BOVINE   DTNQV——K——L——IV——QEAGW—E————A————V——V
         10        20        30        40        50

HUMAN    VLTAA(N)(C)MDESKKLLVRLCEYDLRRWEKWELDLDIKEVFVNPNYSKTTD
BOVINE   ——V——L—S—R————I————M—S————V————II——T—S—
         60        70        80        90        100

HUMAN    N(D)IALLHLAQPATLSQTIVPICLPDSGLAERELNQAGQETLVTGWGYHSS
BOVINE   ——R—K————————————————————S—K—T—V————————RDE
         110       120       130       140       150

HUMAN    REKEAKRNRTFVLNFIKIPVVPHNECSEYMSNNVSENMLCAGILGDRQDA
BOVINE   T————————S——————V————Y—A—VNA—E—KI————————PR
         160       170       180       190       200

HUMAN    CEGD(S)GGPMVASFHGTWFLVGLVSWGEGCGLLHNYGVYTKVSRYLDWIHG
BOVINE   ——————TF—R————————————————R—Y————————————Y—
         210       220       230       240       250

HUMAN    HIRDKEAPQKSWAP
BOVINE   ——KAQ——LE—QPV
         250       260
```

FIG._8.

HYBRID PROTEIN C

This is a Continuation of application of Ser. No. 07/515,378, filed Apr. 27, 1990, now abandoned, which is a continuation in part B Ser. No. 07/458,856, filed Dec. 29, 1989, now abandoned.

FIELD OF THE INVENTION

The present invention relates generally to blood proteins and, more particularly, to compositions of human-like protein C molecules having increased resistance to inactivation by human plasma and thus improved pharmacokinetics in vivo, and methods for producing such compositions.

BACKGROUND OF THE INVENTION

Protein C in its activated form plays an important role in regulating blood coagulation. The activated protein C, a serine protease, inactivates coagulation Factors Va and VIIIa by limited proteolysis. The coagulation cascade initiated by tissue injury, for example, is prevented from proceeding in an unimpeded chain-reaction beyond the area of injury by protein C.

Protein C is synthesized in the liver as a single chain precursor polypeptide which is subsequently processed to a light chain of about 155 amino acids ($M_r$=21,000) and a heavy chain of 262 amino acids ($M_r$=40,000). The heavy and light chains circulate in the blood as a two-chain inactive protein, or zymogen, held together by a disulfide bond. When a 12 amino acid residue is cleaved from the amino-terminus of the heavy chain portion of the zymogen in a reaction mediated by thrombin, the protein becomes activated. Another blood protein, referred to as "protein S," is believed to somehow accelerate the protein C-catalyzed proteolysis of Factor Va.

Protein C has also been implicated in the action of tissue-type plasminogen activator (Kisiel and Fujikawa, *Behring Inst. Mitt.* 73:29–42, 1983 ). Infusion of bovine activated protein C (APC) into dogs results in increased plasminogen activator activity (Comp and Esmon, *J. Clin. Invest.* 68:1221–1228, 1981). Other studies (Sakata et al., *Proc. Natl. Acad. Sci. USA* 82:1121–1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators. APC treatment also results in a dose-dependent decrease in anti-activator activity. In addition, studies with monoclonal antibodies against endogenous APC (Snow et al. FASEB Abstracts, 1988) implicate APC in maintaining patency of arteries during fibrinolysis and limiting the extent of tissue infarct.

Experimental evidence indicates that activated protein C may be clinically useful in the treatment of thrombosis. Several studies with baboon models of thrombosis have indicated that APC in low doses will be effective in prevention of fibrin deposition, platelet deposition and loss of circulation (Gruber et al., *Hemostasis and Thrombosis* 374a: abstract 1353, 1987; Widrow et al., *Fibrinolysis* 2 suppl. 1: abstract 7, 1988; Griffin et al., *Thromb. Haemostasis* 62: abstract 1512, 1989). The use of APC bypasses the need for in vivo activation of protein C, thus providing a faster acting therapeutic agent.

In addition, exogenous activated protein C has been shown to prevent the coagulopathic and lethal effects of gram negative septicemia (Taylor et al., *J. Clin. Invest.* 19:918–925, 1987). Data obtained from studies with baboons suggest that activated protein C plays a natural role in protecting against septicemia.

Protein C may be purified from clotting factor concentrates (Marlar et al., *Blood* 59:1067–1072, 1982) or from plasma (Kisiel, *J. Clin. Invest.* 64:761–769, 1979) and activated in vitro, but the resulting product may be contaminated with such infectious agents as hepatitis virus, cytomegalovirus, or human immunodeficiency virus (HIV).

More recently, methods for producing activated protein C through recombinant DNA technology have been described. Foster et al. (published European Patent Application EP 215,548) disclose the production of activated protein C through the use of cultured mammalian cells transfected with a protein C DNA sequence from which the coding sequence for the activation peptide has been deleted. Foster et al. (EP 266,190) disclose the production of recombinant activated protein C using a DNA sequence encoding an APC precursor with a modified cleavage site.

Moreover, native human activated protein C (either plasma-derived or recombinant) has a relatively short half-life when administered in vivo (about twenty minutes), necessitating the inconvenience of large doses or frequent administration.

Despite the advances in activated protein C production made possible by the use of genetic engineering, yields remain low and the protein is subject to degradation and/or inactivation during the production process. Thus, there remains a need in the art for methods that enable the production of active activated protein C at higher levels and especially the production of molecules which have a substantially increased half-life in vivo. Quite surprisingly, the present invention fulfills these and other related needs.

SUMMARY OF THE INVENTION

Novel compositions comprising protein C having a light chain and a human-like heavy chain are provided. The protein C may be in either its zymogen or activated form. The activated protein C which has a human-like heavy chain will generally be more resistant to inactivation by human plasma factors, such as human alpha-1-antitrypsin, when compared to unaltered, naturally occurring protein C. The compositions are particularly useful in methods for treating patients when they are formulated into pharmaceutical compositions, where they may be given prophylactically or therapeutically to individuals suffering from a variety of disease states. Among the medical indications are protein C deficiencies, which may be an inherited disorder or an acquired condition. Other acquired disease states which may be treated with the novel protein C molecules described herein include, e.g., deep vein thrombosis, pulmonary embolism, stroke, and myocardial infarction. In the latter, protein C may be administered with tissue plasminogen activator to enhance in vivo fibrinolysis, and may be given after the occluding coronary thrombus is dissolved to prevent reocclusion.

Typically, the light chain of the novel protein C molecule will be substantially human, and the human-like heavy chain will comprise at least about 200 amino acids from a human protein C heavy chain sequence, which sequence is generally about 262 residues in the zymogen form and generally about 250 residues in the activated form. In certain preferred embodiments the non-human residues of the human-like heavy chain originate from bovine sequences. The bovine heavy chain sequence substitutions for the human heavy chain sequence regions include substituting Gln-Glu-Ala-Gly-Trp for human amino acid sequence Lys-Met-Thr-Arg- Arg; bovine sequence Arg-Asp-Glu-Thr for human sequence His-Ser-Ser-Arg-Glu-Lys-Glu-Ala; bovine sequence Tyr-Asn-Ala-Cys-Val-His-Ala-Met-Glu-Asn-Lys-Ile is substituted for human amino acid sequence His-Asn-Glu-Cys-Ser-Glu-Val-Met-Ser-Asn-Met-Val; and the bovine region Lys-Ala-Gln-Glu-Ala-Pro-Leu-Glu-Ser-Gln-Pro-Val is substituted for human heavy chain region Arg-Asp-Lys-Glu-Ala-Pro-Gln-Lys-Ser-Trp-Ala-Pro. Of course, it will be understood that certain minor substitutions, insertions or deletions may be made in the human heavy chain framework or non-human regions, so long as the protein C molecule retains biological activity. Desirably, such protein C analogs will have, e.g., increased resistance to inactivation by human plasma and thus a longer plasma half-life or increased biological activity.

In another embodiment the invention concerns a recombinant chimeric protein C molecule having light and heavy chain polypeptides, where the light chain is substantially human and the heavy chain is substantially that of a mammal other than human, preferably bovine. This form of protein C will have substantially the activity of human protein C, but will be more resistant to inactivation by human plasma factors than the naturally occurring human protein C. The sequence of the heavy chain of this embodiment may be substantially homologous to the bovine heavy chain sequence of FIG. 8; a preferred composition has an amino terminal amino acid of the human activated heavy chain (Leu), while the remainder of the heavy chain is substantially bovine.

In another aspect the invention relates to a polynucleotide molecule comprising four operatively linked sequence coding regions which encode, respectively, a pre-pro peptide and a gla domain of a vitamin K-dependent plasma protein, a gla domain-less human protein C light chain, a peptide comprising one or more cleavage sites, and a human-like protein C heavy chain. The protein C molecule expressed by this polynucleotide is biologically active, that is, in its activated form it is capable of inactivating human plasma Factors Va or VIIIa, yet itself has increased resistance to inactivation by human factors such as alpha-1-antitrypsin. To express the protein C molecule the nucleotide sequences are transfected into mammalian cell lines, such as BHK, BHK 570 and 293, and may be cotransfected with sequences which encode endopeptidases reactive at the cleavage sites, such as the KEX2 gene of *Saccharomyces cerevisiae*.

BRIEF DESCRIPTION OF THE FIGURES

FIG. 1 illustrates the nucleotide sequence of a human protein C cDNA and the inferred amino acid sequence of the protein. Negative numbers refer to the pre-pro peptide. Positive numbers refer to the sequence of the mature zymogen. Diamonds indicate consensus N-linked glycosylation sites. The arrow indicates the junction between the activation peptide and the activated protein C heavy chain.

DESCRIPTION OF THE SPECIFIC EMBODIMENTS

Novel compositions of protein C are provided which are suitable for administration to humans. Because of the pivotal role protein C plays in the coagulation cascade, acting in its activated form as an anticoagulant, it has a variety of important therapeutic applications. The novel compositions described herein provide a possibility of achieving an extended half-life and stability in vivo not achievable with prior compositions of protein C purified from human plasma or produced by recombinant means.

In one aspect of the invention, the composition comprises a hybrid, or chimeric, protein C molecule where the amino acid sequence of the light chain is substantially human and the sequence of the heavy chain is substantially that of a mammal other than human, such as bovine. It may also be desirable or convenient that the amino-terminal amino acid of the activated heavy chain be from the human sequence, which is typically leucine (Leu). The remainder of the heavy chain may be entirely of the bovine heavy chain sequence. It should be understood that reference herein to "protein C" is meant to include the zymogen and activated forms, unless otherwise specified. Protein C zymogen includes an activation peptide at the amino terminus of the heavy chain. The activation peptide may be the native human activation peptide, the native bovine activation peptide, or a modified activation peptide as disclosed herein.

Figure 8:
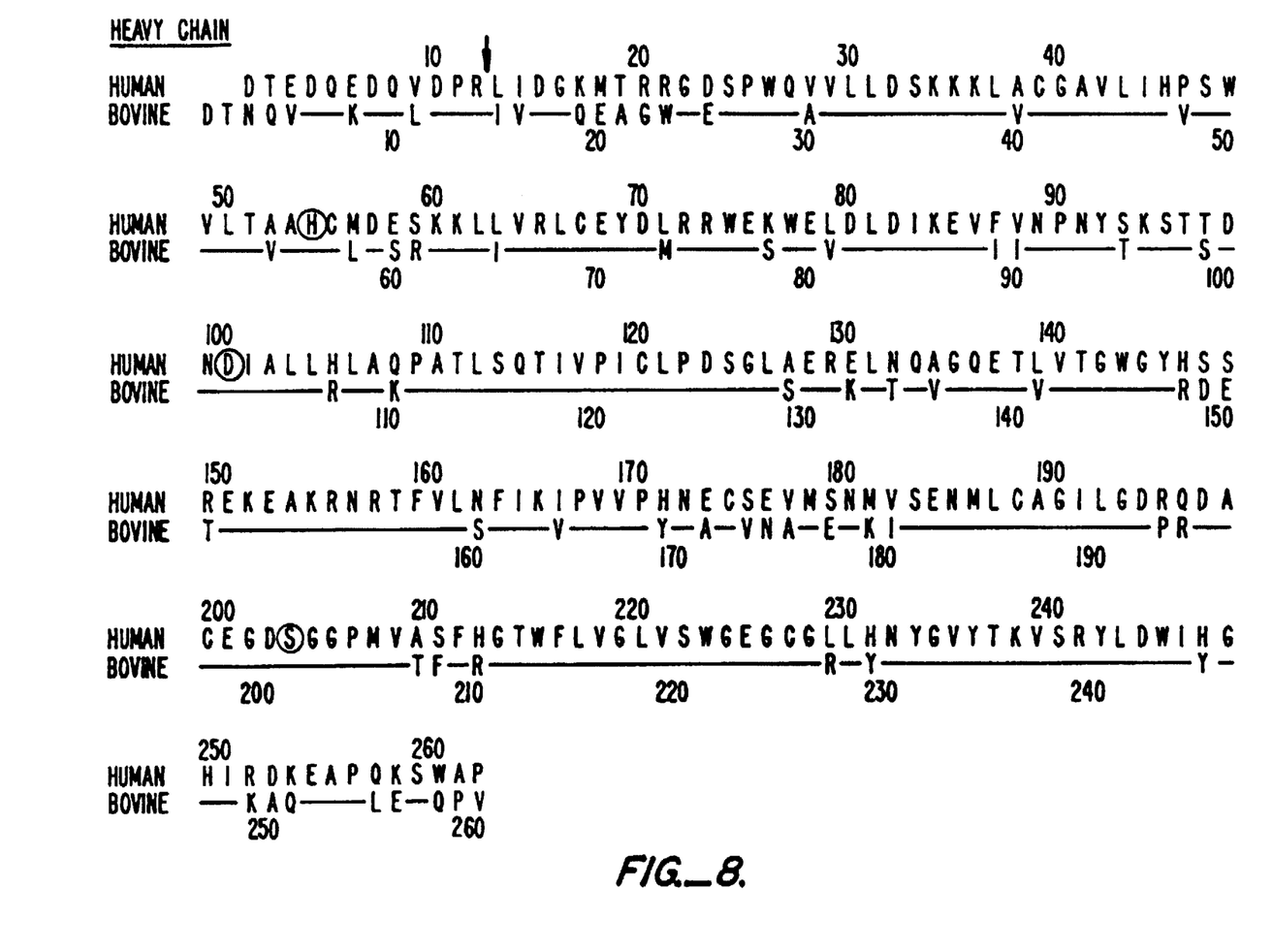
FIG. 8 shows a comparison of the amino acid sequences of the heavy chains of human and bovine protein C. Each sequence is numbered from the first amino acid of the respective heavy chain. The arrow indicates the junction between the activation peptide and the activated protein C heavy chain. Within the bovine sequence, (.) indicates the presence of the same amino acid residue as in the human sequence, and (–) indicates a gap introduced to maximize sequence alignment.

In alternative embodiments, protein C molecules are produced which are human-like in nature, and thus possess generally less immunogenicity than a chimeric molecule. Short sequences, including but not limited to single amino acids, of the human heavy chain (as shown in FIG. 8, for example) may be replaced with the corresponding heavy chain sequences from protein C of a mammal other than human, conveniently bovine sequences. The object is to achieve protein C molecules which are substantially human and, when activated, will have a substantially longer half-life in human blood, thereby necessitating less frequent administration and/or smaller dosages. As used herein, the term "human-like heavy chain" is meant to refer to a protein C heavy chain which is substantially homologous to an authentic human heavy chain, i.e., at least about 75%, and preferably about 85–95% identical, particularly in those regions which are relatively conserved among species, and containing at least one amino acid substitution. In general, it is preferred to retain the interaction of protein C with plasminogen activator inhibitor-1 by retaining the basic amino acid residues at positions 191–193.

The hybrid or human-like protein C is produced by cultured mammalian cells transfected with genes which encode the hybrid or human-like molecules. The cells are transfected with an expression vector comprising a promoter operably linked to a DNA encoding the protein C molecule. The transfected cells are cultured in a medium which permits the expression of the protein, and protein C is then isolated from the medium. The protein C may be produced in its activated or zymogen form. If it is produced in its activated form the medium should be prepared so as to contain a minimal amount of serum, or to be serum-free, as described in commonly owned copending application Ser. No. 07/392,861, incorporated herein by reference.

Cloned DNA sequences encoding human protein C have been described (Foster and Davie, Proc. Natl. Acad. Sci. USA 81:4766–4770, 1984; Foster et al., Proc. Natl. Acad. Sci. USA 82:4673–4677, 1985 and Bang et al., U.S. Pat. No. 4,775,624, each incorporated herein by reference). A cDNA encoding bovine protein C has been described by Long et al., Proc. Natl. Acad. Sci. USA 81:5563–5656, 1984, incorporated herein by reference. In general, cDNA sequences are preferred for use within the present invention due to their lack of intervening sequences which can lead to aberrant RNA processing and reduced expression levels. Complementary DNAs encoding protein C may be obtained from libraries prepared from liver cells of various mammalian species according to standard laboratory procedures. Using probes from bovine or human cDNA, one may identify and clone the DNA encoding protein C of other mammalian species. It will be understood, however, that suitable DNA sequences can also be obtained from genomic clones or can be synthesized de novo according to conventional procedures. If partial clones are obtained, it is necessary to join them in proper reading frame to produce a full length clone, using such techniques as endonuclease cleavage, ligation, and loop-out mutagenesis.

For example, to clone bovine cDNA encoding the protein C heavy chain, a human protein C cDNA fragment may be used to probe a bovine liver cDNA library. The human protein C cDNA fragment may be prepared from human liver mRNA, for example, using conventional methods. Alternatively, probes may be designed based on the published bovine protein C cDNA sequence (Long et al., Proc. Natl. Acad. Sci. USA 81:5653–5656, 1984). A hybrid protein C coding sequence may be constructed by joining the human light chain cDNA to the non-human fragment (e.g., bovine) in proper reading frame to produce a full length protein, using cleavage with appropriate restriction endonucleases, ligation, synthetic oligonucleotides and loop-out mutagenesis.

In alternative embodiments, the entire human protein C coding region may be cloned and selected modifications made to the heavy chain sequence to increase the half-life and stability of the molecule in human plasma by making it resistant to inhibition or inactivation by factors in human plasma. The modifications will be directed to areas of the heavy chain where the amino acid sequence differs substantially among species. Thus, the species-specificity of human alpha-1-antitrypsin for the human heavy chain is used to make site(s) typically recognized by alpha-1-antitrypsin in the heavy chain less susceptible to recognition and thereby inhibit the rate at which the activity of protein C is degraded. With the bovine heavy chain sequence, for example, the following sequences have been identified as sites which may be substituted for corresponding human heavy chain regions (numbering according to Foster et al., Proc. Natl. Acad. Sci. USA 81:4766–4770, 1984 and as shown in FIG. 8):

(1) a bovine heavy chain amino acid sequence Gln-Glu-Ala-Gly-Trp (heavy chain amino acids 19–23), is substituted for human amino acid sequence Lys-Met-Thr-Arg-Arg (heavy chain amino acids 17–21);

(2) bovine heavy chain amino acid sequence Arg-Asp-Glu-Thr (amino acids 148–151), is substituted for human amino acid sequence His-Ser-Ser-Arg-Glu-Lys-Glu-Ala (amino acids 146–153);

(3) bovine heavy chain amino acid sequence Tyr-Asn-Ala-Cys-Val-His-Ala-Met-Glu-Asn-Lys-Ile (amino acids 169–180), is substituted for human amino acid sequence His-Asn-Glu-Cys-Ser-Glu-Val-Met-Ser-Asn-Met-Val (amino acids 171–182); and (4) bovine heavy chain amino acid sequence Lys-Ala-Gln-Glu-Ala-Pro-Leu-Glu-Ser-Gln-Pro-Val (amino acids 249–260) is substituted for human heavy chain residues Arg-Asp-Lys-Glu-Ala-Pro-Gln-Lys-Ser-Trp-Ala-Pro (amino acids 251–262).

It will be understood that preferably as few sequence modifications as possible are made to provide an increased resistance to inactivation by human plasma factors. Desirably, the region of substitution will be as small as possible, such that most preferred will be a single heavy chain amino acid substitution of one species for a corresponding amino acid of the human sequence. Combinations of sequence region substitutions may also be employed. The increased resistance of a molecule to degradation may be readily assayed with well known procedures, such as resistance to alpha-1-antitrypsin or human plasma, as described below. It is important that any such substitutions not substantially decrease the biological activity of protein C. By "biological activity" is meant a function or set of functions performed by activated human protein C in a biological context (i.e., in an organism or an in vitro model thereof). Biological activities of proteins may be divided into catalytic and effector activities. Catalytic activities of vitamin K-dependent plasma proteins, such as protein C, generally involve specific proteolytic cleavages of other plasma proteins, resulting in activation or deactivation of the substrates. Effector activities include specific binding of the biologically active molecules to calcium, phospholipid or other small molecules, to macromolecules, such as proteins, or to cells. Effector activity frequently augments, or is essential to, catalytic activity under physiological conditions. For protein C, biological activity is characterized by the anticoagulant properties of the activated protein. Activated protein C inactivates Factor Va and Factor VIIIa in the presence of acidic phospholipid and calcium. Protein S appears to be involved in the regulation of this function (Walker, ibid.). The catalytic activities of protein C are believed to reside primarily in the heavy chain. These activities may be readily assayed using well known procedures.

To produce recombinant activated protein C directly, the cloned DNA sequence is modified to delete or replace that portion encoding the activation peptide. The resulting DNA sequence will encode a pre-pro peptide, the light chain of protein C, a cleavage site and the heavy chain of activated protein C. The DNA sequence may further encode a spacer peptide between the light and heavy chains.

In one embodiment, the resultant sequence will encode the light and heavy chains of protein C joined by the sequence Lys-Arg. As used herein, the light chain of activated protein C is understood to comprise amino acids 1–149 of the sequence disclosed in FIG. 1 or sequences substantially homologous thereto, or such sequences having C-terminal extensions, generally extensions of one to about six amino acids. The heavy chain of activated protein C is understood not to include the activation peptide (i.e. to begin at amino acid number 170, leucine, as shown in FIG. 1 in the case of human activated protein C).

In a preferred embodiment, the DNA sequence is further modified to include one or more novel cleavage sites between the light and heavy chains. The cleavage site may be in the form of the amino acid sequence $(R_1)_n$-$R_2$-$R_3$-$R_4$, wherein $R_1$ through $R_4$ are lysine (Lys) or arginine (Arg) and n is an integer between 0 and 3. Particularly preferred sequences include Arg-Arg-Lys-Arg, Lys-Arg-Lys-Arg and Lys-Lys-Arg. Alternatively, the cleavage site may be of the form $R_1$-$R_2$-$R_3$-$R_4$-X-$R_5$-$R_6$-$R_7$-$R_8$, wherein each of $R_1$ through $R_8$ is Lys or Arg and X is a peptide bond or a spacer peptide of 1 to 12 amino acids. Spacer peptides useful in this regard include the amino acid sequences Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln, Asp-Gln, Asn-Ile-Leu-Asn, and the native protein C activation peptide having the amino acid sequence Asp-Thr-Glu-Asp-Gln-Glu-Asp-Gln-Val-Asp-Pro-Arg. A third group of cleavage site modifications includes the substitution of amino acid residue 154 (His) of native human protein C with an amino acid residue selected from the group consisting of Lys, Arg and Leu to give a cleavage site sequence of the general formula Y-Z-$R_1$-$R_2$, wherein Y is Lys, Arg or Leu; $R_1$ and $R_2$ are Lys or Arg; and Z is an amino acid other than Lys or Arg, preferably Leu. Representative cleavage-site mutants which may be useful in the present invention are shown below in Table I. Cleavage sites 829, 1058, 1645, 1880, 1953, 1954, 1962, 2043, 2155 and 2274 are useful in directly producing activated protein C.

TABLE I

| Amino Acid Sequences of Cleavage-Site Mutants | | |
|---|---|---|
| 149 | 150 | 170 |
| 594 (Wild-type Human Protein C) | | |
| E-K-K-R-S-H-L- | K-R-D-T-E-D-Q-E-D-Q-V-D-P- | R-L-I- D- |
| 829 | | |
| E-K- K-R-S-H-L- | K-R- | L- |
| 962 | | |
| E-K- K-R S-H-L-R-R-K-R-D-T-E-D-Q-E-D-Q-V-D-P- R-L- | | |
| 1058 | | |
| E-K- K-R-S-H-L-R-R-K-R- | | L- |
| 1645 | | |
| E-K- K-R-S-H-L-R-R-K-R-D-T-E-D-Q-E-D-Q-R-R-K-R-L- | | |
| 1880 | | |
| E-K- K-R-S-H-L-R-R-K-R-D-T- | D-Q-R-R-K-R-L- | |
| 1953 | | |
| E-K- K-R-S-H-L-R-R-K-R- | R-R-K-R-L- | |
| 1954 | | |
| E-K- K-R-S-H-L-R-R-K-R-D- | Q-R-R-K-R-L- | |
| 1962 | | |
| E-K- K-R- | | L- |
| 2043 | | |
| E-K-R-K-R | | L- |
| 2155 | | |
| E-K- K-R-S-H-L-R-R-K-R- N-I- L-N- D-Q-R-R-K-R-L- | | |
| 2274 | | |
| E-K- K-R- | | A-N-S- R-R-K-R-L- |

Modification of the DNA sequence may be obtained by site-specific mutagenesis. Techniques for site-specific mutagenesis are well known in the art and are described by, for example, Zoller and Smith (DNA 3:479–488, 1984). Alternatively, the wild-type protein C sequence may be enzymatically cleaved to remove the native activation peptide sequence, and the sequences encoding the heavy and light chains joined to a synthesized DNA sequence encoding one of the cleavage sites described above.

As will be understood by those skilled in the art, variants and analogs of protein C may also be produced in the context of the compositions and methods of the present invention. Variants and analogs of protein C include those containing minor amino acid changes, such as those due to genetic polymorphism, and those in which amino acids have been inserted, deleted and/or substituted without substantially decreasing the biological activity of the protein. Protein C analogs further include proteins that have the protein C amino-terminal portion (gla domain) substituted with a gla domain of one of the vitamin-K dependent plasma proteins Factor VII, Factor IX, Factor X, prothrombin or protein S. The gla domain spans approximately 35–45 amino acid residues at the amino termini of these proteins, with a C-terminal boundary generally corresponding to an exon-intron boundary in the respective gene. The gla domain of human protein C extends from amino acid number 1 of the mature light chain to approximately amino acid number 37.

DNA sequences for use within the present invention will encode a pre-pro peptide at the amino-terminus of the hybrid protein C molecule to obtain proper post-translational processing (e.g. gamma-carboxylation of glutamic acid residues) and secretion from the host cell. The pre-pro peptide may be that of protein C or another vitamin K-dependent plasma protein, such as Factor VII, Factor IX, Factor X, prothrombin or protein S. It is generally preferred that the pre-pro peptide and gla domain be obtained from the same protein.

The DNA sequence encoding the hybrid protein C is inserted into a suitable expression vector, which vector is then used to transfect cultured mammalian cells. Expression vectors for use in carrying out the present invention will comprise a promoter capable of directing the transcription of a cloned gene or cDNA. Preferred promoters include viral promoters and cellular promoters. Viral promoters include the SV40 promoter (Subramani et al., *Mol. Cell. Biol.* 1:854–864, 1981) and the CMV promoter (Boshart et al., *Cell* 41:521–530, 1985). A particularly preferred viral promoter is the major late promoter from adenovirus 2 (Kaufman and Sharp, *Mol. Cell. Biol.* 2:1304–1319, 1982). Cellular promoters include the mouse kappa gene promoter (Bergman et al., *Proc. Natl. Acad. Sci. USA* 81:7041–7045, 1983) and the mouse $V_H$ promoter (Loh et al., *Cell* 33:85–93, 1983). A particularly preferred cellular promoter is the mouse metallothionein-I promoter (Palmiter et al., *Science* 222:809–814, 1983). Expression vectors may also contain a set of RNA splice sites located downstream from the promoter and upstream from the insertion site for the protein C sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nuc. Acids Res.* 9:3719–3730, 1981) or the polyadenylation signal from the human protein C gene or the bovine protein C gene. The expression vectors may also include a noncoding viral leader sequence, such as the adenovirus 2 tripartite leader, located between the promoter and the RNA splice sites; and enhancer sequences, such as the SV40 enhancer and the sequences encoding the adenovirus VA RNAs.

Cloned DNA sequences are introduced into cultured mammalian cells by, for example, calcium phosphate-mediated transfection (Wigler et al., *Cell* 14:725–732, 1978; Corsaro and Pearson, *Somatic Cell Genetics* 7:603–616, 1981; Graham and Van der Eb, *Virology* 52d:456–467, 1973) or electroporation (Neumann et al., *EMBO J.* 1:841–845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (*Mammalian Cell Technology*, Butterworth Publishers, Stoneham, Mass., incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1–2 days, to begin expressing the gene of interest. As used herein the term "appropriate growth medium" means a medium containing nutrients and other components required for the growth of cells and the expression of the protein C gene. Media generally include a carbon source, a nitrogen source, essential amino acids, essential sugars, vitamins, salts, phospholipids, protein and growth factors. For production of gamma-carboxylated protein C, the medium will contain vitamin K, preferably at a concentration of about 0.1 µg/ml to about 5 µg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of protein C.

Preferred mammalian cell lines for use in the present invention include the COS-1 (ATCC CRL 1650), baby hamster kidney (BHK) and 293 (ATCC CRL 1573; Graham et al., *J. Gen. Virol.* 36:59–72, 1977) cell lines. Preferred BHK cell lines include the tk⁻ ts13 BHK cell line (Waechter and Baserga, *Proc. Natl. Acad. Sci. USA* 79:1106–1110, 1982, incorporated herein by reference), hereinafter referred to as BHK 570 cells. The BHK 570 cell line has been deposited with the American Type Culture Collection, 12301 Parklawn Dr., Rockville, Md. 20852 on Dec. 20, 1989 under ATCC accession number CRL 10314. A tk⁻ ts13 BHK cell line is also available from the ATCC under accession number CRL 1632. In addition, a number of other cell lines may be used within the present invention, including Rat Hep I (ATCC CRL 1600), Rat Hep II (ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216–4220, 1980).

Processing of activated protein C precursors by cleavage after a Lys-Arg dipeptide between the light and heavy chains may be enhanced by introducing the *S. cerevisiae* KEX2 gene into the host cell, as described in published European patent application EP319,944. The KEX2 gene encodes an endopeptidase that cleaves after a dibasic amino acid sequence (Fuller et al., in Leive, ed., *Microbiology* 1986, 273–278). A cultured mammalian cell line stably transfected with this gene is thus useful for expressing activated protein C.

Protein C produced according to the present invention may be purified by affinity chromatography on an anti-protein C antibody column. The use of calcium-dependent monoclonal antibodies, as described by Wakabayashi et al. (*J. Biol. Chem.* 261:11097–11108, 1986), is particularly preferred. Additional purification may be achieved by conventional chemical purification means, such as liquid chromatography. Other methods of purification, including barium citrate precipitation, are known in the art, and may be applied to the purification of the novel protein C described herein (see, generally, Scopes, R., *Protein Purification*, Springer-Verlag, N.Y. (1982). Substantially pure protein C of at least about 90 to 95% homogeneity is preferred, and 98 to 99% or more homogeneity most preferred, for pharmaceutical uses. Once purified, partially or to homogeneity as desired, the protein C may then be used therapeutically.

The protein C molecules of the present invention and pharmaceutical compositions thereof are particularly useful for administration to humans to treat a variety of conditions involving intravascular coagulation. For instance, although deep vein thrombosis and pulmonary embolism can be treated with conventional anticoagulants, the protein C described herein may be used to prevent the occurrence of thromboembolic complications in identified high risk patients, such as those undergoing surgery or those with congestive heart failure. Since activated protein C is more selective than heparin, being active in the body generally when and where thrombin is generated and fibrin thrombi are formed, protein C will be more effective and less likely to cause bleeding complications than heparin when used prophylactically for the prevention of deep vein thrombosis. The dose of protein C for prevention of deep vein thrombosis is in the range of about 100 µg to 100 mg/day, preferably 1 to 10 mg/day, and administration should begin at least about 6 hours prior to surgery and continue at least until the patient becomes ambulatory. In established deep vein thrombosis and/or pulmonary embolism, the dose of protein C ranges from about 100 µg to 100 mg as a loading dose followed by maintenance doses ranging from 3 to 300 mg/day. Because of the lower likelihood of bleeding complications from protein C infusions, protein C can replace or lower the dose of heparin during or after surgery in conjunction with thrombectomies or embolectomies.

The protein C compositions of the present invention will also have substantial utility in the prevention of cardiogenic emboli and in the treatment of thrombotic strokes. Because of its low potential for causing bleeding complications and its selectivity, protein C can be given to stroke victims and may prevent the extension of the occluding arterial thrombus. The amount of protein C administered will vary with each patient depending on the nature and severity of the stroke, but doses will generally be in the range of those suggested below.

Pharmaceutical compositions of activated protein C provided herein will be a useful treatment in acute myocardial infarction because of the ability of activated protein C to enhance in vivo fibrinolysis. Activated protein C can be given with tissue plasminogen activator or streptokinase during the acute phases of the myocardial infarction. After the occluding coronary thrombus is dissolved, activated protein C can be given for subsequent days or weeks to prevent coronary reocclusion. In acute myocardial infarction, the patient is given a loading dose of at least about 1–500 mg of activated protein C, followed by maintenance doses of 1–100 mg/day.

The protein C of the present invention is useful in the treatment of disseminated intravascular coagulation (DIC), in either its zymogen or activated form. Patients with DIC characteristically have widespread microcirculatory thrombi and often severe bleeding problems which result from consumption of essential clotting factors. Because of its selectivity, protein C will not aggravate the bleeding problems associated with DIC, as do conventional anticoagulants, but will retard or inhibit the formation of additional microvascular fibrin deposits.

As the novel protein C molecules provided herein generally have a longer half-life than authentic human protein C, a significant use of these compositions is the treatment of people who have an inherited protein C deficiency. Such patients, who may be homozygous or heterozygous for the deficiency, may suffer from severe thrombosis. They are presently maintained on Factor IX concentrates, which contain protein C. For treatment of the homozygous deficient individuals, assuming an average blood plasma volume of about 3,000 ml and allowing for some diffusion into the extravascular space, protein C of the invention may be administered one or more times daily at levels of from 1–300 mg daily. Heterozygotes for protein C deficiency will generally require lower maintenance doses than homozygotes.

The pharmaceutical compositions are intended for parenteral, topical, oral or local administration for prophylactic and/or therapeutic treatment. Preferably, the pharmaceutical compositions are administered parenterally, i.e., intravenously, subcutaneously, or intramuscularly. Thus, this invention provides compositions for parenteral administration which comprise a solution of the protein C molecules dissolved in an acceptable carrier, preferably an aqueous carrier. A variety of aqueous carriers may be used, e.g., water, buffered water, 0.4% saline, 0.3% glycine and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of protein C in these formulations can vary widely, i.e., from less than about 0.5%, usually at or at least about 1% to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 10 mg of protein C. Actual methods for preparing parenterally administrable compounds will be known or apparent to those skilled in the art and are described in more detail in for example, *Remington's Pharmaceutical Science*, 16th ed., Mack Publishing Company, Easton, Pa. (1982), which is incorporated herein by reference.

The compositions containing the protein C molecules or a cocktail thereof can be administered for prophylactic and/or therapeutic treatments. In therapeutic applications, compositions are administered to a patient already suffering from a disease, as described above, in an amount sufficient to cure or at least partially arrest the disease and its complications. An amount adequate to accomplish this is defined as "therapeutically effective dose." Amounts effective for this use will depend on the severity of the disease or injury and the general state of the patient, but generally range from about 1 mg to about 300 mg of protein C per day, with dosages of from about 5 mg to about 25 mg of protein C per day being more commonly used. It must be kept in mind that the materials of the present invention may generally be employed in serious disease or injury states, that is, life-threatening or potentially life threatening situations. In such cases, in view of the minimization of extraneous substances and the prolonged half-life of protein C in human plasma made feasible by this invention, it is possible and may be felt desireable by the treating physician to administer substantial excesses of these protein C compositions.

In prophylactic applications, compositions containing the hybrid protein C are administered to a patient susceptible to or otherwise at risk of a disease state or injury to enhance the patient's own anticoagulative or fibrinolytic capabilities. Such an amount is defined to be a "prophylactically effective dose." In this use, the precise amounts again depend on the patient's state of health and general level of endogenous protein C, but generally range from about 0.5 mg to about 250 mg per 70 kilogram patient, especially about 1 mg to about 25 mg per 70 kg. of body weight.

Single or multiple administrations of the compositions can be carried out with dose levels and pattern being selected by the treating physician. For ambulatory patients requiring daily maintenance levels, the protein C may be administered by continuous infusion using a portable pump system, for example. In any event, the pharmaceutical formulations should provide a quantity of protein C of this invention sufficient to effectively treat the patient.

The following examples are offered by way of illustration of the invention and not by limitation.

EXAMPLE I

Construction of Human-Bovine Hybrid Protein C

This Example describes the construction of a hybrid protein C coding sequence encoding a hybrid protein C having a human Pre-Pro sequence, a human light chain, a human activation peptide and the first amino acid of the human activated protein C heavy chain, followed by the remainder of the bovine protein C heavy chain sequence. Following secretion from the host cell and activation, the protein comprises the human protein C light chain which is disulfide bonded to a heavy chain containing the first amino acid (leucine) of the human heavy chain followed by the bovine heavy chain sequence from the second amino acid (valine). The hybrid molecule is shown in the Examples which follow to have increased resistance to inactivation by α-1-antitrypsin and other human plasma factors.

A. Bovine Heavy Chain cDNA Cloning

Bovine cDNA encoding the protein C heavy chain was cloned from a bovine liver cDNA λgt11 library (obtained from Clontech, Palo Alto, Calif. 94301) by probing the library with a random-primed human protein C cDNA fragment.

1. Preparation of human protein C cDNA probe

A cDNA sequence coding for a portion of human protein C was prepared as described by Foster and Davie (ibid.). Briefly, a λgt11 cDNA library was prepared from human liver mRNA by conventional methods. Clones were screened using an $^{125}$I-labeled affinity-purified antibody to human protein C, and phage were prepared from positive clones by the plate lysate method (Maniatis et al., *Molecular Cloning: A Laboratory Manual*, Cold Spring Harbor, 1982, incorporated herein by reference), followed by banding on a cesium chloride gradient. The cDNA inserts were removed using Eco RI and were subcloned into plasmid pUC9 (Vieira and Messing, *Gene* 19:259–268, 1982). Restriction fragments were subcloned in phage vectors M13mp10 and M13mp11 (Messing, *Meth. Enzymol.* 101:20–77, 1983) and were sequenced by the dideoxy method (Sanger et al., *Proc. Natl. Acad. Sci. USA* 74:5464–5467, 1977). A clone that contained DNA corresponding to the known partial sequence of human protein C (Kisiel, ibid., 1979) and encoded protein C beginning at amino acid 64 of the light chain and extending through the heavy chain and into the 3' non-coding region was selected. This clone was designated λHC1375. A second cDNA clone coding for protein C from amino acid 24 was also identified. The insert from the larger clone was subcloned into pUC9 and the plasmid was designated pHCλ6L. This clone encodes a major portion of protein C, including the heavy chain coding region, termination codon, and 3' non-coding region.

The cDNA insert from λHC1375 was nick translated using $\alpha$-$^{32}$P dNTP's and used to probe a human genomic library in phage λCharon 4A (Maniatis et al., *Cell* 15:687–702, 1978) using the plaque hybridization procedure of Benton and Davis (*Science* 196:181–182, 1977) as modified by Woo (*Meth. Enzymol.* 68:381–395, 1979). Positive clones were isolated and plaque-purified (Foster et al., *Proc. Natl. Acad. Sci. USA* 82:4673–4677, 1985, herein incorporated by reference). Phage DNA prepared from positive clones (Silhavy et al., in *Experiments with Gene Fusion*, Cold Spring Harbor Laboratory, 1984) and was digested with Eco RI or Bgl II and the genomic inserts were purified and subcloned in pUC9. (Restriction fragments of the genomic inserts were subcloned into M13 vectors and sequenced to confirm their identity and establish the DNA sequence of the entire gene.)

The cDNA insert of pHCλ6L was nick translated and used to probe the phage λCharon 4A library. One genomic clone was identified that hybridized to probes made from the 5' and 3' ends of the cDNA. This phage clone was digested with Eco RI, and a 4.4 kb fragment, corresponding to the 5' end of the protein C gene, was subcloned into pUC9. The resultant recombinant plasmid was designated pHCR4.4. Complete DNA sequence analysis revealed that the insert in pHCR4.4 included two exons of 70 and 167 base pairs separated by an intron of 1263 bp. The first exon encodes amino acids –42 to –19; the second encodes amino acids –19 to 37. Sequence analysis confirmed the DNA sequence of the entire protein C gene.

A genomic fragment containing an exon corresponding to amino acids –42 to –19 of the pre-pro peptide of protein C was isolated, nick translated, and used as a probe to screen a cDNA library constructed by the technique of Gubler and Hoffman (*Gene* 25:263–269, 1983) using mRNA from Hep G2 cells. This cell line was derived from human heptocytes and was previously shown to synthesize protein C (Fair and Bahnak, *Blood* 64: 194–204, 1984). Ten positive clones comprising cDNA inserted into the Eco RI site of phage λgt11 were isolated and screened with an oligonucleotide probe corresponding to the 5' non-coding region of the protein C gene. One clone was also positive with this probe and its entire nucleotide sequence was determined. The cDNA contained 70 bp of 5' untranslated sequence, the entire coding sequence for human pre-pro-protein C, and the entire 3' non-coding region corresponding to the second polyadenylation site. The cDNA sequence and the encoded amino acid sequence are shown in FIG. 1.

Figure 2:
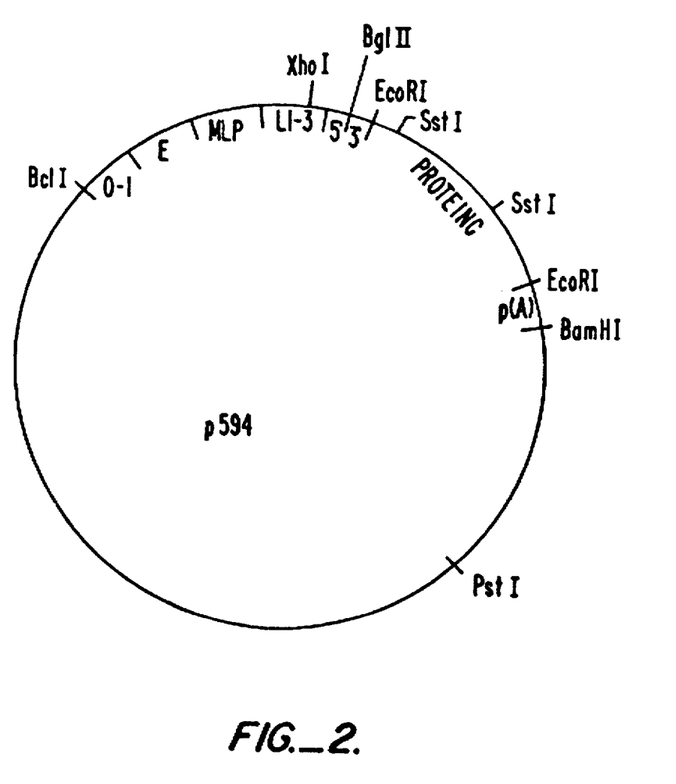
FIG. 2 depicts the protein C expression vector p594. Symbols used are 0–1, the adenovirus 5 0–1 map unit sequence; E, the SV40 enhancer; MLP, the adenovirus 2 major late promoter; L1-3, the adenovirus 2 tripartite leader; 5', 5' splice site; 3', 3' splice site; p(A), the SV40 late polyadenylation signal.

The protein C cDNA was isolated as an Eco RI fragment and cloned into the vector pDX (Hagen et al., U.S. Pat. No. 4,784,950, incorporated herein by reference) as disclosed in published European patent application EP 266,190, incorporated herein by reference. Recombinant plasmids were screened by restriction analysis to identify those having the protein C insert in the correct orientation with respect to the promoter elements, and plasmid DNA (designated pDX/PC) was prepared from a correct clone. Because the cDNA insert in pDX/PC contained an ATG codon in the 5' non-coding region, oligonucleotide-directed deletion mutagenesis was performed on the cDNA to remove the three base pairs. The resulting vector, designated p594, contained the protein C cDNA operably linked to the adenovirus 2 major late promoter (FIG. 2). This vector also contained the adenovirus 5 origin of replication (0–1 map units sequence), the SV40 enhancer, the adenovirus 2 tripartite leader, a set of RNA splice sites, an SV40 polyadenylation signal and a dihydrofolate reductase gene as a selectable marker.

2. Isolation of bovine cDNA clone

Using a random-primed 1.7 kb Eco RI fragment from p594 containing the human protein C cDNA, a bovine liver cDNA λgt11 library was probed for protein C cDNA. A bovine clone was identified and recovered as an Eco RI fragment and was cloned into pUC9. The resultant plasmid was cut with Taq I and Eco RI, and the fragment encoding the protein C heavy chain was recovered.

B. Preparation of Human Protein C Light Chain cDNA

To obtain a human light chain cDNA for ultimately joining to the bovine Taq I-Eco RI fragment, an appropriate restriction fragment was prepared from a DNA sequence (designated PC962) which encoded the human protein C. The PC962 DNA was generated from p594, described above, and contained a DNA sequence encoding two additional arginine residues at the junction between the light chain and the activation peptide of protein C (Table I). The cloned human cDNA in p594 was altered by site-specific mutagenesis (essentially as described by Zoller and Smith, *DNA* 3:479–488 (1984)), using the mutagenic oligonucleotide ZC962 (5' AGT CAC CTG AGA AGA AAA CGA GAC A 3') and oligonucleotide ZC550 (5' TCC CAG TCA CGA CGT 3'). Plasmid p594 was digested with Sst I, the approximately 840 bp fragment was cloned into M13mp11, and single-stranded template DNA was isolated. Following mutagenesis, a correct clone was identified by sequencing. Replicative form DNA was isolated and digested with Sst I to isolate the mutagenized fragment. This fragment was joined with Sst I-cut p594 in a two-part ligation. Clones having the Sst I fragment inserted in the desired orientation were identified by restriction enzyme mapping. The resulting expression vector was designated pDX/PC962.

Figure 3:
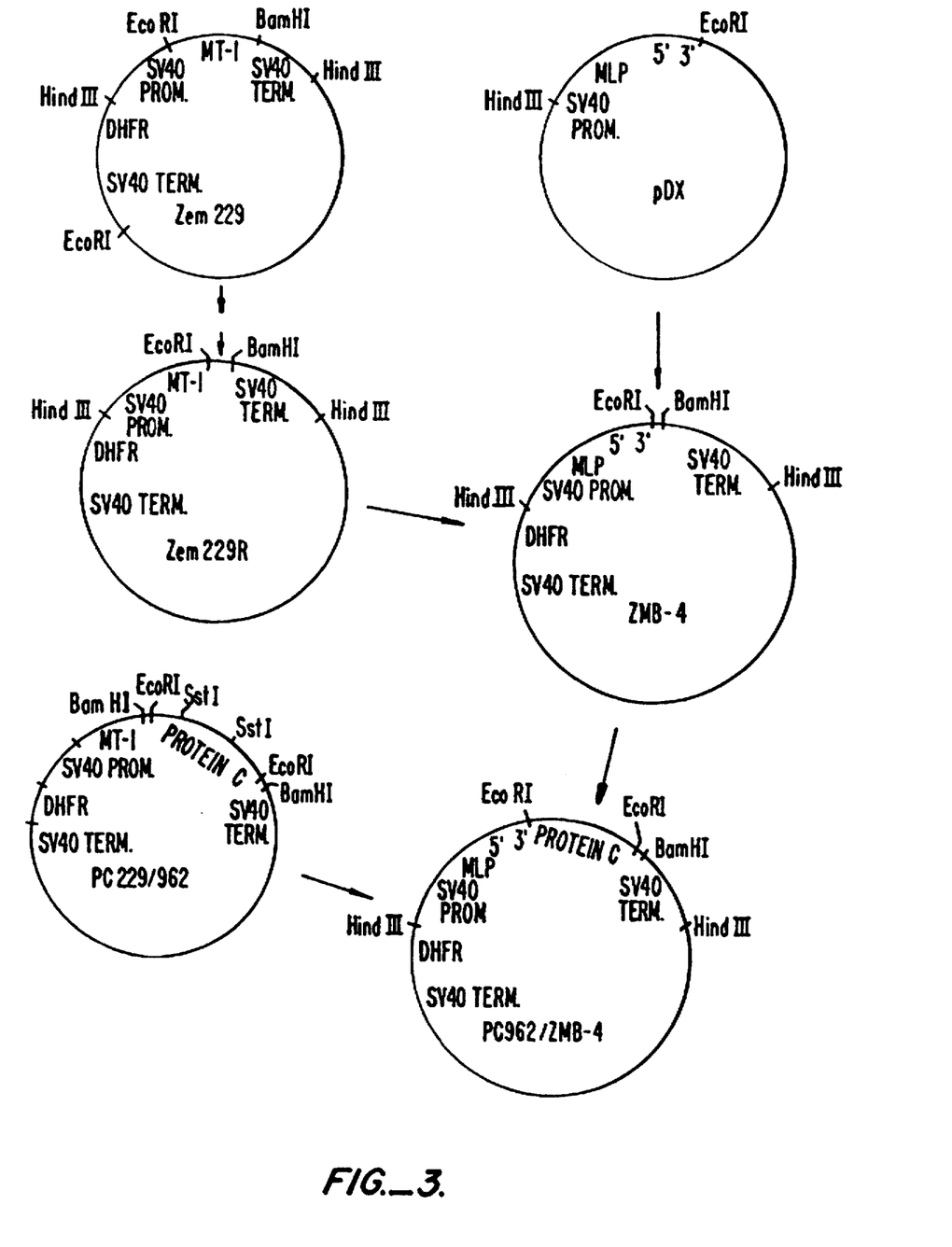
FIG. 3 illustrates the construction of the protein C expression vector PC962/ZMB-4.

A second expression vector, designated PC229/962, was constructed by inserting the PC962 cDNA into plasmid Zem229. Zem229 is a pUC18-based expression vector containing a unique Bam HI site for insertion of foreign DNA between the mouse metallothionein-I promoter and SV40 transcription terminator. Zem229 also contains an expression unit of the SV40 early promoter, mouse dihydrofolate reductase gene, and SV40 terminator. An Eco RI fragment containing the PC962 cDNA from pDX/PC962 was joined, via Eco RI-Bam HI synthetic oligonucleotide adapters, to Zem229, which had been cut with Bam HI and treated with phosphatase. The resulting vector, designated PC229/962, is illustrated in FIG. 3.

Expression vector PC962/ZMB-4 was constructed from Zem229, pDX (Hagen et al., U.S. Pat. No. 4,784,950, incorporated herein by reference) and the PC962 DNA sequence.

Zem229 was modified to convert the Bam HI cloning site to an Eco RI site. The plasmid was first modified to delete its two Eco RI sites by partial digestion with Eco RI, blunting with DNA polymerase I (Klenow fragment) and dNTPs, and religating. The resulting plasmid was digested with Bam HI and ligated with synthetic Bam HI-Eco RI adapters. The resulting plasmid was designated Zem229R. Zem229R was digested with Hind III and Eco RI, and the 520 bp fragment containing the SV40 and MT-1 promoters was removed. The large fragment of Zem229R was then joined to the ~1100 bp Hind III-Eco RI fragment of pDX, which contains the SV40 promoter/enhancer, the adenovirus major late promoter, and a set of splicing signals to construct ZMB-4 (FIG. 3). The PC962 sequence was isolated from PC229/962 as an Eco RI fragment, which was then inserted into ZMB-4 to construct PC962/ZMB-4 (FIG. 3).

C. Construction of Hybrid Protein C Coding Sequence

Figure 4:
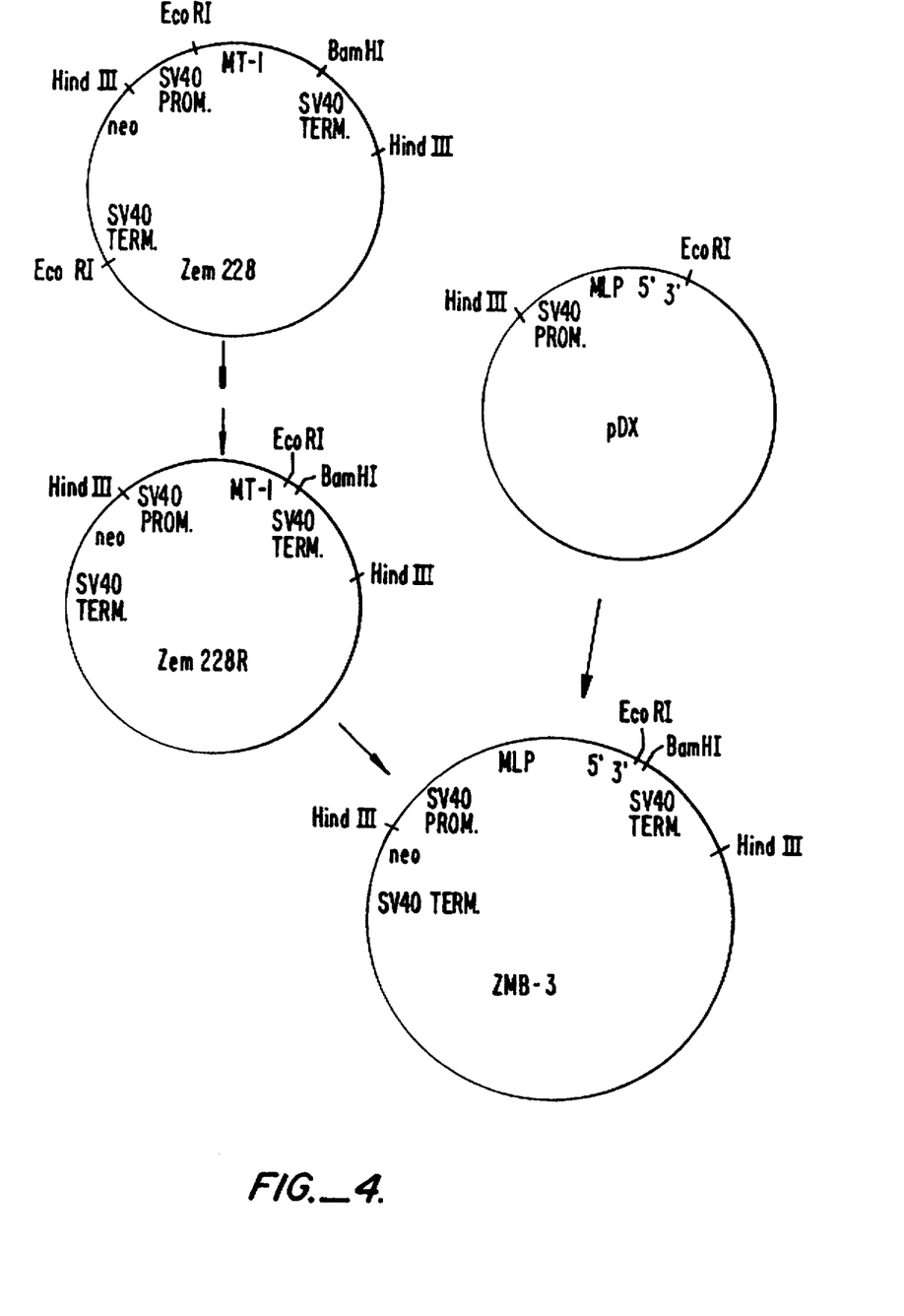
FIG. 4 illustrates the construction of the vector ZMB-3.

The human-bovine protein C coding sequence was constructed by joining an Eco RI-Sst II fragment of human light chain cDNA (from PC962/ZMB-4) to a Taq I-Eco RI fragment of bovine heavy chain cDNA using a synthetic linker. The linker was constructed by annealing oligonucleotides ZC2228 (5'GGCTCGT 3') and ZC2229 (5'CGCCGAGCAGC 3'). The hybrid protein encoded by the resultant sequence has the amino acid sequence of human protein C through the first amino acid of the heavy chain followed by the remainder of the bovine heavy chain: (H Pre-pro)-(H L-chain)-cleavage site (RRKR)-(H activation peptide)-Leu-(B H chain), where the sequence at the human-bovine junction is:

The hybrid cDNA was assembled by joining the cDNA fragments and linker with Eco RI-digested vector ZMB-3 in a four-part ligation. Expression vector ZMB-3 was constructed from Zem228 (EP 319,944) and pDX (Hagen et al., U.S. Pat. No. 4,784,950, incorporated by reference herein). Zem228 is a pUC18-based expression vector containing a unique Bam HI site for insertion of foreign DNA between the mouse metallothionein-I promoter and SV40 transcription terminator. Zem228 also contains an expression unit comprising the SV40 early promoter, the neomycin resistance gene, and the SV40 terminator. Thus, in Zem228 the inserted gene is under the control of the metallothionein-Ipromoter and SV40 terminator, and the vector can be selected with the antibiotic neomycin. Zem228 was modified to delete its two Eco RI sites by partial digestion with Eco RI, blunting with DNA polymerase I (Klenow fragment) and dNTPs, religation, digestion with Bam HI and ligation with Bam HI-Eco RI adapters to construct plasmid Zem228R. Zem228R was digested with Hind III and Eco RI, and the 520 bp fragment containing the SV40 and MT-1 promoters was removed. The large fragment of Zem228R was then joined to the ~1100 bp Hind III-Eco RI fragment of pDX, which contains the SV40 promoter/enhancer, the adenovirus major late promoter, and a set of splicing signals. The resultant vector was designated ZMB-3 (FIG. 4).

The ZMB-3 vector containing the hybrid human-bovine protein C coding sequence was transfected into tk$^{13}$ ts13 BHK cells (ATCC CRL 1632). Transfectants were selected in Dulbecco's modified Eagle's Medium (DMEM) containing 10% fetal bovine serum and 500 µg/ml G-418. Conditioned media were harvested, and the recombinant protein C was purified by immunoaffinity chromatography on a PCL-2-Sepharose column. This column was prepared by coupling a monoclonal antibody (designated PCL-2) specific for the $Ca^{++}$-bound light chain of protein C to CNBr-activated Sepharose (Pharmacia, Piscataway, N.J.). The samples were applied to the column in the presence of 10 mM $CaCl_2$. The column was washed with 50 mM Tris HCl, 1.0M NaCl, 10 mM $CaCl_2$, pH 7.5. Protein C was eluted from the column with 15 mM EDTA in 50 mM Tris-HCl, pH 7.5.

EXAMPLE II

Resistance of Hybrid Protein C to Inactivation

The ability of a protein C inhibitor, α-1-antitrypsin, to inhibit activated bovine protein C (obtained from Enzyme Research Labs, South Bend, Ind.) and immuno-affinity purified, activated recombinant human protein C (from baby hamster kidney cells transfected with pDX/PC962) was compared with the inhibition of the activated human-bovine protein C hybrid. To activate the protein C molecules, each was combined with protein C activator from Agkistrodon contortrix contortrix (ACC-C obtained from W. Kisiel, Univ. of New Mexico; see, Kisiel et al., *J. Biol. Chem.* 262:12607–12613 (1987)).

To assay resistance to inactivation, a 200 µl solution of each protein (50 µg/ml in TBS [50 mM Tris pH 7.5, 150 mM NaCl]+15 mM EDTA) was combined with 60 ng ACC-C and 5 µl BSA (50 mg/ml). The mixtures were incubated at 37° C. for 90 minutes. A 20 µl sample of each activated protein C was combined with 5 µl BSA (50 mg/ml) and 0, 20, 40, or 80 µl of 1 mg/ml α-1-antitrypsin (Sigma Chemical Company, St. Louis, Mo.) in TBS to a final reaction volume of 105 µl. The mixtures were incubated at 37° C. for 18 ½ hours, then 20 µl of each sample was combined with 80 µl of 1 mM chromogenic substrate (#336 Spectrozyme PCa, obtained from American Diagnostica) and incubated at room temperature for approximately ten minutes. Color development was measured at 405 nm.

Figure 5:
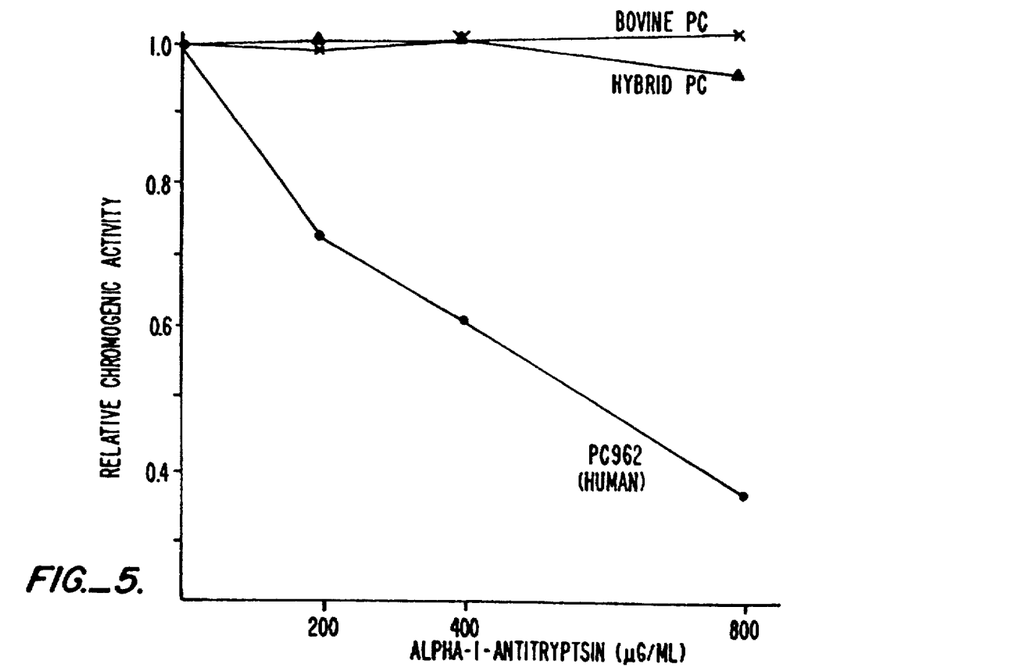
FIG. 5 illustrates the results of chromogenic activity assays on human, bovine, and hybrid protein C molecules. Data for each protein are normalized to 100% activity in the absence of alpha-1-antitrypsin.

The results, shown in FIG. 5, indicate that while activated human protein C was readily inactivated by α-1-antitrypsin, both the bovine and bovine-human hybrid were resistant to inactivation.

EXAMPLE III

Resistance of Hybrid Protein C to Inactivation by Human Plasma

The inactivation of bovine-human protein C and human protein C (PC962) by human plasma was examined. The experiments were performed substantially as outlined in Example II, with the following modifications.

The bovine-human hybrid protein C and PC962 human protein C were activated by incubating 7.5 µg of each, or a BSA control, with 375 ng ACC-C in 100 µl of TBS/BSA for 90 minutes at 370°. Twenty microliter samples of activated protein C were added to wells of 96-well microtiter plates, then 0, 5, 10 or 20 µl of citrated human plasma was added to each well. The sample volumes were adjusted to 100 µl with TBS/BSA, and the plates were incubated overnight (16 hours) at 37° C. The assays were developed by removing 20 µl (in duplicate) from each sample and adding them to 80 µl chromogenic substrate (0.75 mM). The absorbance at 405 nm was determined after incubating for about ten minutes at room temperature.

Figure 6:
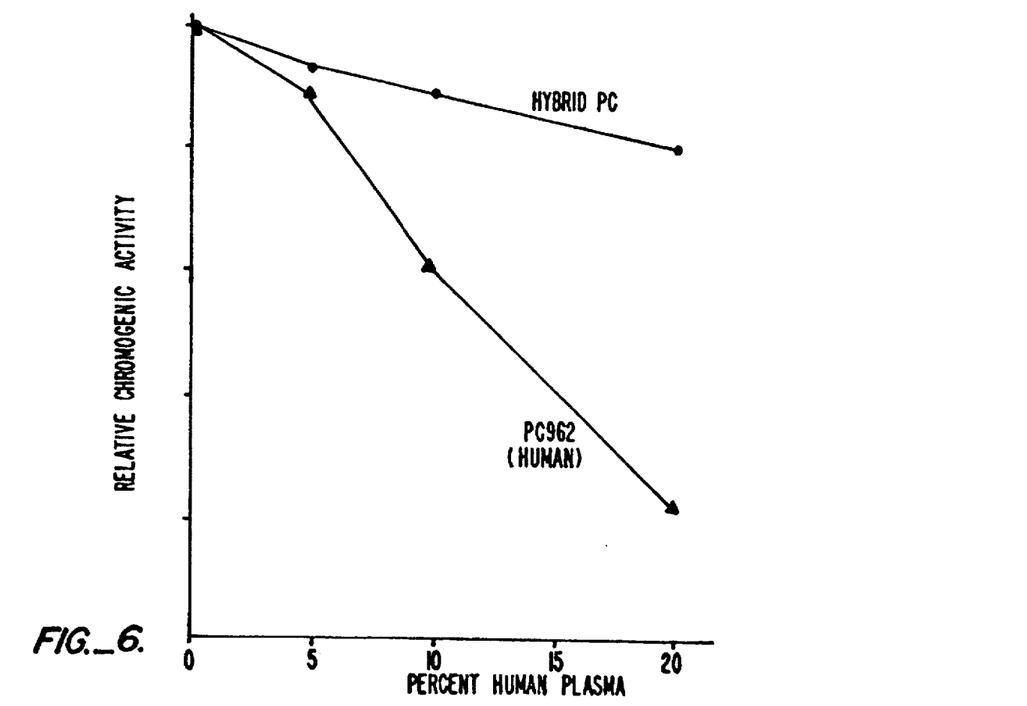
FIG. 6 illustrates the inactivation of human and hybrid protein C molecules by human plasma. Results are normalized for each protein.

The results, shown in FIG. 6, indicate that the activity of human protein C decreased much more rapidly than that of the hybrid protein C when the proteins were exposed to human plasma. The activated hybrid protein C appeared to have about three times greater chromogenic activity than the activated human protein C in the absence of plasma. The hybrid protein also appeared to have a half-life about four times greater than the human protein.

The rates of inactivation of hybrid and human protein C molecules by human plasma were then compared. The assays were performed substantially as described above, using 7.5 μg of PC962 or hybrid protein C activated overnight (18 hours) with 37.5 ng ACC-C in 100 μl TBS/BSA at 37° C. A 10 μl sample from each was withdrawn and added to 190 μl TBS/BSA. The mixtures were placed on ice, then 250 μl citrated human plasma was added to each, and the assays were incubated at 37° C. Samples (20 μl ) were withdrawn at 0, 105, 185 and 240 minutes and added to 80 μl chromogenic substrate, and the absorbance at 405 nm determined as above.

Figure 7:
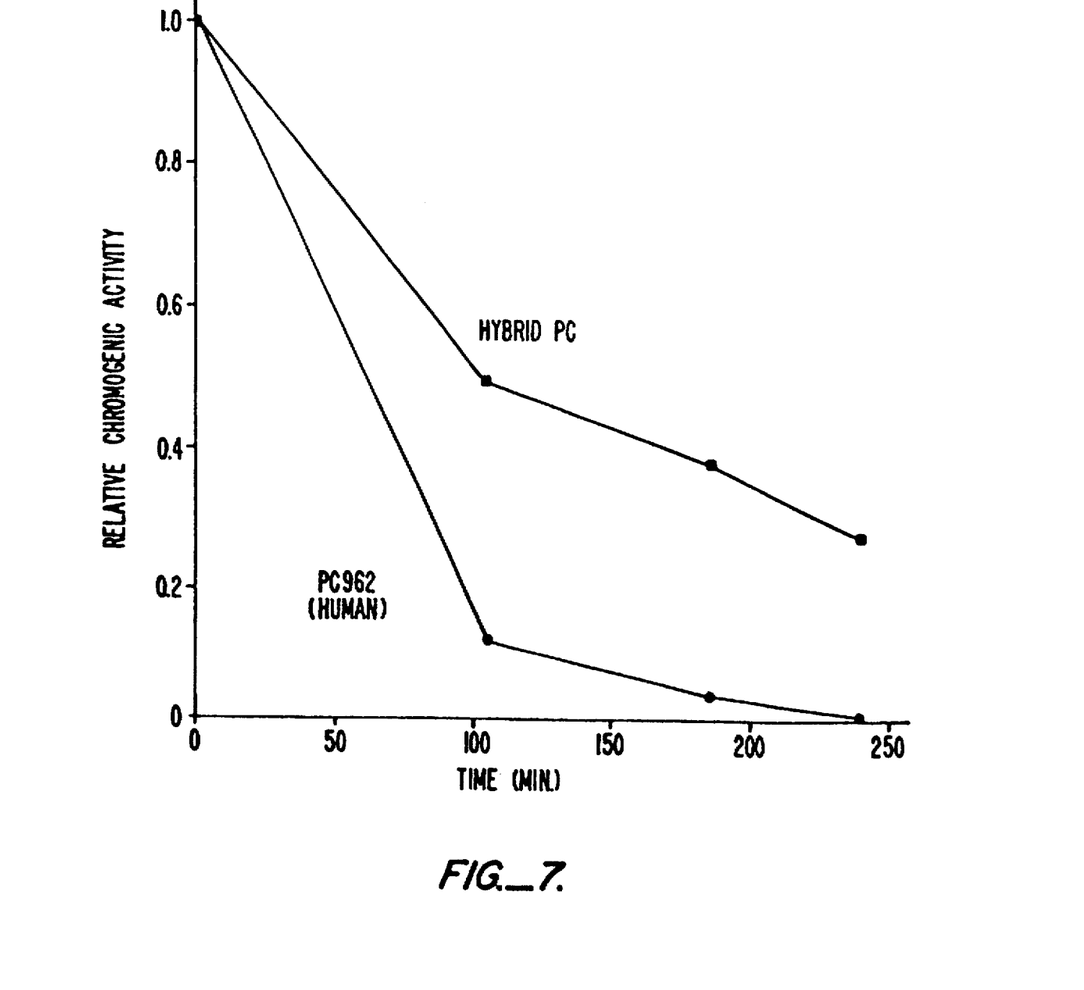
FIG. 7 illustrates the time course of inactivation of human and hybrid protein C molecules by human plasma. Results are normalized for each protein.

The results, shown in FIG. 7, suggest that the half-life of the hybrid protein C in human plasma was about three times that of the human activated protein C. The hybrid protein and human activated protein C had approximately equivalent anticoagulant activity in human plasma. This suggests that the bovine-human hybrid protein C will be particularly useful in treating humans, in that lower or less frequent doses of protein C will need to be administered to a patient, thereby decreasing the cost and inconvenience of therapy to the patient.

EXAMPLE IV

Anticoagulant Activity of Hybrid Protein C

The anticoagulant activity of the activated hybrid protein C molecule of Example I was compared to that of native human APC in the APTT assay. Two micrograms of isolated hybrid protein C or recombinant PC962 were combined with 50 ng ACC-C in 100 μl of TBS. The mixtures were incubated at 37° C. for one hour, then combined with 100 μl of normal human plasma and 100 μl Actin FS (Dade, Miami, Fla.). The resulting mixtures were incubated at 37° C. for 100 seconds, then 100 μl of activated protein C in TBS was added. After an additional 100 seconds at 37° C., 100 μl of 1M CaCl$_2$ was added to each sample, and the clotting times were measured. Results, shown in Table II, indicated that the hybrid protein C has anticoagulant activity in human plasma comparable to that of the native human protein.

TABLE II

| | Clotting Time (Seconds) | |
|---|---|---|
| APC(np) | PC962 | Hybrid |
| 0 | 51 | 51 |
| 20 | 64.6 | 62.8 |
| 40 | 73.6 | 69.2 |
| 60 | 83.6 | 76.7 |
| 80 | 84.9 | 82.3 |
| 100 | 88.4 | 90.3 |

EXAMPLE V

Bovine Sequence Substitutions Into Human Heavy Chain

A. Substitutions in Zymogen Protein C

To produce a protein C molecule with a substantially human heavy chain and having increased stability and increased half-life in human plasma when compared to authentic human activated protein C, sequences of bovine protein C heavy chain are substituted for corresponding sequences of the human heavy chain.

One modification of the human heavy chain involves the substitution of bovine heavy chain amino acids Gln-Glu-Ala-Gly-Trp (amino acids 19–23; numbering according to Foster et al., Proc. Natl. Acad. Sci. USA 81: 4766–4770 (1984), incorporated herein by reference and as shown in FIG. 8) for amino acids Lys-Met-Thr-Arg-Arg in the human heavy chain (amino acids 17–21; numbering according to Foster et al., id. and as shown in FIG. 8). To encode the substituted amino acids, site specific mutagenesis was employed with the synthetic oligonucleotide ZC2451 (5' CTC ATT GAT GGG CAG GAG GCT GGA TGG GGA GAC AGC CC 3'). The protein C Sst I fragment of pDX/PC962 (Example I) was cloned into vector M13mp10 (Messing, Meth. Enzymol. 101:20–77 (1983), incorporated herein by reference). Single-stranded template DNA was prepared as above and subjected to site directed mutagenesis using the oligonucleotide ZC2451, essentially as described by Zoller and Smith, DNA 3:479–488 (1984), incorporated herein by reference, using the two primer method with oligonucleotide ZC550. Positive clones were selected and sequenced to confirm the mutagenesis. The mutagenized sequence was recovered from replicative form DNA as a Pst I-Sst I fragment. This fragment was joined, in a four-part ligation, with a ~592 bp Eco RI-Pst I fragment from plasmid PC962/ZMB-4 (comprising the 5' protein C coding sequence), a ~700 bp Sst I-Eco RI fragment from plasmid PC962/ZMB-4 (comprising the 3' protein C coding sequence), and Eco RI-digested and phosphatased ZMB-4. Plasmids were screened for correct insert orientation by restriction enzyme digestion. A correct plasmid was selected and used to transfect tk⁻ ts13 BHK cells (ATCC CRL 1632) by calcium phosphate co-precipitation, as described in Example I. Transfectants producing protein C were selected at 500 nM methotrexate at 2–3 days post-transfection, and cell-conditioned media were prepared. The modified protein C was purified from the culture supernatant as described above. The sensitivity of the modified protein C to inactivation by alpha-1-antitrypsin and human plasma factors is assayed as described in Examples II and III.

Another modification of the human heavy chain, made either separately or in conjunction with other substitutions described herein, is the substitution of bovine amino acids Arg-Asp-Glu-Thr (heavy chain residues 148–151) for human heavy chain amino acids His-Ser-Ser-Arg-Glu-Lys-Glu-Ala (human heavy chain residues 146–153) using the synthetic oligonucleotide ZC2452 (5' GCT GGG GCT ACA GAG ACG AGA CCA AGA GAA ACC GC 3'). The Sst I-Eco RI fragment of pDX/PC962 (Example I) was cloned into vector M13mp10. Single-stranded template DNA was prepared and subjected to site directed mutagenesis with ZC2452 using the two primer method as described above. Positive clones were selected and sequenced to confirm the substitution. The mutagenized Sst I-Eco RI fragment was then reisolated from phage replicative form DNA and joined, in a four-part ligation, to a ~330 bp Eco RI-Sal I fragment from plasmid PC962/ZMB-4 (comprising the 5' protein C sequence), a ~730 bp Sal I-Sst I fragment from plasmid PC962/ZMB-4 (comprising the middle portion of the protein C sequence), and Eco RI-digested and phosphatased ZMB-4. Plasmids were screened for correct insert orientation by restriction enzyme digestion, and a correct construction was selected. Transfection was performed as described above and protein C containing the modified site was harvested from conditioned medium of the successful transfectants. The sensitivity of the heavy chain modified protein C to inactivation is compared to that of unmodified protein C as described.

A substitution of the bovine sequence Tyr-Asn-Ala-Cys-Val-His-Ala-Met-Glu-Asn-Lys-Ile (heavy chain amino acids 169–180) for the human heavy chain sequence His-Asn-Glu-Cys-Ser-Glu-Val-Met-Ser-Asn-Met-Val (human heavy chain residues 171–182) is used to provide enhanced resistance of the protein C molecule to inactivation. The Sst I-Eco RI fragment of pDX/PC962 was cloned into vector M13mp10, single-stranded template DNA was prepared and then subjected to site directed mutagenesis with synthetic oligonucleotide ZC2453 (5' CGT GGT CCC GTA CAA TGC ATG TGT CCA TGC CAT GGA AAA CAA GGT GTC TGA GAA C 3') using the two primer method as described above. As above, positive clones were selected and sequenced to confirm mutagenesis. The Sst I-Eco RI fragment is then reisolated from the replicative form DNA and is combined, in a four-part ligation, with the ~592 bp Eco RI-Pst I fragment from PC962/ZMB-4, the ~460 bp Pst I-Sst I fragment from PC962/ZMB-4, and Eco RI-digested and phosphatased ZMB-4. A vector containing the protein C sequence in the correct orientation is then transfected into appropriate mammalian host cells and the transfectants are cultured.

Amino acid residues 249–260 of the bovine protein C heavy chain (Lys-Ala-Gln-Glu-Ala-Pro-Leu-Glu-Ser-Gln-Pro-Val) are substituted using site directed mutagenesis for human heavy chain residues 251–262 (Arg-Asp-Lys-Glu-Ala-Pro-Gln-Lys-Ser-Trp-Ala-Pro). The Sst I-Eco RI protein C fragment of pDX/PC962 was cloned into vector M13mp10, single-stranded template DNA was prepared and subjected to site directed mutagenesis with synthetic oligonucleotide ZC2454 (5' GGG CAC ATC AAA GCT CAG GAG GCC CCT CTT GAG AGC CAG GTG CCT TAG CGA CCC 3') using the two primer method as described above. Positive clones were selected and sequenced to confirm mutagenesis, and the mutagenized Sst I-Eco RI fragment was reisolated from replicative form (RF) DNA. The mutagenized fragment was then used to construct an expression vector for the zymogen form of protein C. The vector was constructed by ligating the mutagenized RF fragment, the ~592 bp Eco RI-Pst I fragment from PC962/ZMB-4, the ~460 bp Pst I-Sst I fragment from PC962/ZMB-4, and Eco RI-digested and phosphatased ZMB-4. The resulting vector is then used to transfect tk$^{31}$ ts3 BHK cells as described above. Successful transfectants are identified and cultured, and cell-conditioned medium is prepared. Increased resistance of the modified protein C to inactivation by α-1-antitrypsin or human plasma factors, compared to that of unmodified human protein C, is assayed as described above.

B. Substitutions in Activated Protein C

A DNA sequence encoding an activated protein C precursor with the cleavage site sequence Arg-Arg-Lys-Arg was constructed by mutagenesis of the wild-type protein C sequence. The resultant sequence (designated 1058) was analogous to that encoding PC962 but lacked the portion encoding the activation peptide. The amino acid sequence at the junction between the light and heavy chains of the 1058 protein is presented in Table 1.

The protein C sequence present in plasmid p594 was altered in a single mutagenesis to delete the codons for the activation peptide and insert the Arg-Arg codons at the processing site. A mutagenesis was performed according to standard procedures on the 870 bp Sst I fragment from p594 cloned into an M13 phage vector using oligonucleotides ZC1058 (5' CGC AGT CAC CTG AGA AGA AAA CGA CTC ATT GAT GGG 3') and ZC550 (5' TCC CAG TCA CGA CGT 3').

A DNA sequence encoding an activated protein C precursor having the linker sequence Lys-Lys-Arg-Ala-Asn-Ser-Arg-Arg-Lys-Arg between the light (amino acids 1–149) and heavy chains designated PC2274 (Table 1).

To construct the PC2274 sequence, the PC1058 Sst I fragment was inserted into M13mp10 and mutagenized according to standard procedures with the oligonucleotide ZC2274 (5' GAG AAG AAG CGC GCC AAC TCC AGA AGA AAA CGA CT 3'). The mutagenized RF DNA was digested with Pst I and Sst I and the ~430 bp fragment was recovered.

The activated protein C expression vector was constructed by ligating the ~430bp Pst I-Sst I fragment from the PC2274 RF, the ZC2454-mutagenized Sst I-Eco RI fragment (Example V.A), the ~592 bp Eco RI-Pst I fragment from PC962/ZMB-4 and Eco RI-digested and phosphatased ZMB-4. A vector having the desired insert orientation was identified by restriction enzyme digestion and was used to transfect tk$^-$ts13 BHK cells as described above.

It is evident from the above results that compositions are provided having substantially the activity of human protein C while possessing a resistance to inactivation by α-1-antitrypsin and human plasma factors. These results are especially encouraging, in that modified protein C molecules may now be employed as therapeutic or prophylactic compositions which have an increased stability in human plasma and, accordingly, an increased half-life when compared to preparations of human protein C purified from plasma or produced by recombinant means. The efficacy, convenience and economics of lower dosages and less frequent administration are among the advantages conferred by the compositions of the present invention.

Although the foregoing invention has been described in some detail by way of illustration and example for purposes of clarity of understanding, it will be obvious that certain changes and modifications may be practiced within the scope of the appended claims.

What is claimed is:

1. A polynucleotide molecule comprising four operatively linked sequence coding regions encoding, respectively a pre-pro peptide and a gla domain of a vitamin K-dependent plasma protein, a gla domain-less human protein C light chain, a peptide comprising a cleavage site at its C-terminus and adjacent to the N-terminus of a human-like heavy chain of activated protein C comprising at least 200 amino acids which correspond to the human activated protein C heavy chain sequence, with remaining amino acid substitutions from the bovine activated protein C heavy chain, wherein the bovine amino acid substitutions are effective for providing a biologically active protein C molecule upon cleavage at said C-terminal site, and said substitutions are effective in increasing the resistance of the protein to inactivation by human plasma or alpha-1-antitrypsin when compared to naturally occurring activated human protein C.

2. The polynucleotide molecule according to claim 1, wherein at least one of the bovine heavy chain sequences is amino acids 19–23, Gln-Glu-Ala-Gly-Trp; amino acids 148–151, Arg-Asp-Glu-Thr; or amino acids 169–180, Tyr-Asn-Ala-Cys-Val-His-Ala-Met-Glu-Asn-Lys-Ile; and is substituted for human heavy chain amino acids 17–21, Lys-Met-Thr-Arg-Arg; amino acids 146–153, His-Ser-Ser-Arg-Glu-Lys-Glu-Ala; or amino acids 171–182, His-Asn-Glu-Cys-Ser-Glu-Val-Met-Ser-Asn-Met-Val; respectively, where amino acid numbers correspond to those of FIG. 8.

3. The polynucleotide molecule according to claim 1, wherein the peptide comprising a cleavage site comprises $R_1$-$R_2$-$R_3$-$R_4$-x-$R_5$-$R_6$-$R_7$-$R_8$, wherein each of $R_1$-$R_8$ is Lys or Arg and x is a peptide bond or spacer peptide of 1–12 amino acids.

4. The polynucleotide sequence according to claim 1, wherein the peptide comprising a cleavage site comprises $(R_1)_n$-$R_2$-$R_3$-$R_4$, wherein each of $R_1$, $R_2$, $R_3$, and $R_4$ is Lys or Arg and n=0, 1, 2 or 3.

5. The polynucleotide molecule of claim 4, wherein $(R_1)_n$-$R_2$-$R_3$-$R_4$ is Arg-Arg-Lys-Arg.

6. A mammalian cell line transfected with the polynucleotide molecule of claim 1.

7. The transfected cell line of claim 6, wherein the cell line is a baby hamster kidney cell line or 293 cell line.

8. The transfected cell line of claim 6, wherein the cell line is BHK 570, ATCC No. CRL 10314.

9. The mammalian cell line of claim 6, wherein the cell line is cotransfected with a KEX2 gene of Saccharomyces cerevisiae which gene encodes an endopeptidase.

10. A polynucleotide comprising four operatively linked sequence coding regions encoding, respectively, a pre-pro peptide and a gla domain of a vitamin K-dependent plasma protein, a gla domain-less human protein C light chain, a peptide comprising a clevage site at its C-terminus and adjacent to the N-terminus of a bovine heavy chain of activated protein C, wherein upon expression said polynucleotide encodes a biologically active protein C molecule when cleaved at said cleavage site having increased resistance to inactivation by human plasma or alpha-1-antitrypsin when compared to naturally occurring activated' human protein C.

11. The polynucleotide according to claim 10, wherein the bovine sequence corresponds to that of FIG. 8.

12. The polynucleotide according to claim 10, wherein the amino terminal amino acid encoded by the heavy chain sequence is Leu.

* * * * *